(12) United States Patent
Deliencourt-Godefroy et al.

(10) Patent No.: US 9,062,313 B2
(45) Date of Patent: Jun. 23, 2015

(54) GEM-DIFLUORINATED C-ISOPROPYLGALACTOSIDE DERIVATES

(75) Inventors: Géraldine Deliencourt-Godefroy, Boise D'Ennebourg (FR); Hyacinthe Fillon, Saint Etienne du Rouvray (FR)

(73) Assignee: TFCHEM, Val de Reuil (FR)

( * ) Notice: Subject to any disclaimer, the term of this patent is extended or adjusted under 35 U.S.C. 154(b) by 0 days.

(21) Appl. No.: 14/237,490

(22) PCT Filed: Aug. 8, 2012

(86) PCT No.: PCT/EP2012/065547
§ 371 (c)(1),
(2), (4) Date: Feb. 6, 2014

(87) PCT Pub. No.: WO2013/021018
PCT Pub. Date: Feb. 14, 2013

(65) Prior Publication Data
US 2014/0199727 A1     Jul. 17, 2014

(30) Foreign Application Priority Data

Aug. 8, 2011  (EP) .................................... 11306021

(51) Int. Cl.
| | | |
|---|---|---|
| C12N 15/72 | (2006.01) | |
| C12P 21/00 | (2006.01) | |
| C12N 15/63 | (2006.01) | |
| C07D 309/10 | (2006.01) | |
| C07H 7/02 | (2006.01) | |

(52) U.S. Cl.
CPC ............ *C12N 15/635* (2013.01); *C07D 309/10* (2013.01); *C12N 15/72* (2013.01); *C07H 7/02* (2013.01); *C12P 21/00* (2013.01)

(58) Field of Classification Search
None
See application file for complete search history.

(56) References Cited

U.S. PATENT DOCUMENTS

| | | |
|---|---|---|
| 2006/0142206 A1 | 6/2006 | Quirion et al. |
| 2009/0138675 A1 | 5/2009 | Marr et al. |
| 2009/0311203 A1 | 12/2009 | Castelot Deliencourt-Godefroy et al. |

FOREIGN PATENT DOCUMENTS

| | | |
|---|---|---|
| WO | WO-2004/014928 A2 | 2/2004 |
| WO | WO-2004/094445 A1 | 11/2004 |
| WO | WO-2007/125194 A1 | 11/2007 |
| WO | WO-2007/125203 A1 | 11/2007 |

OTHER PUBLICATIONS

Benhaddou et al., "Tetra-*n*-propylammonium tetra-oxoruthenate (VII): a reagent of choice for the oxidation of diversely protected glycopyranoses and glycofuranoses to lactones," Carbohydrate Research, 1994, vol. 260, pp. 243-250.
Bessmertnykh et al., "Palladium-catalyzed oxidation of benzylated aldose hemiacetals to lactones," Carbohydrate Research, 2004, vol. 339, pp. 1377-1380.
Burkhart et al., "C-Glycosides: A Stereoselective Synthesis of α- and β-C-Galactosides with Glycosyl Dianions," Tetrahedron Letters, 1998, vol. 39, pp. 7699-7702.
Carpintero et al., "Stereospecific Synthesis of α- and β-C-Glycosides from Glycosyl Sulfoxides: Scope and Limitations," J. Org. Chem., 2001, vol. 66, pp. 1768-1774.
Chiara et al., "Samarium Diiodide-Mediated Reductive Coupling of Epoxides and Carbonyl Compounds: A Stereocontrolled Synthesis of C-Glycosides from 1,2-Anhydro Sugars," Agnew. Chem. Int. Ed. 2002, vol. 41 No. 17, pp. 3242-3246.
Chorki et al., "First Synthesis of 10 α-(Trifluoromethyl)deokoartemisinin," Organic Letters, 2002, vol. 4, No. 5, pp. 757-759.
Cuenca et al., "Addition of Ethyl Bromodifluoroacetate to Lactones: Reactivity and Stereoselectivity," Synlett, 2005, No. 17, pp. 2627-2630.
Donovan et al., "Review: Optimizing inducer and culture conditions for expression of foreign proteins under the control of the *lac* promoter," Journal of Industrial Microbiology, 1996, vol. 16, pp. 145-154.
Frey et al., "179. Preparation and Transmetallation of a Triphenylstannyl β-$_D$-Glucopyranoside: A Highly Stereoselective Route to β-$_D$-Glycosides via Glycosyl Dianions," Helvetica Chimica Acta, 1994, vol. 77, pp. 2060-2069.
Gilbert et al., "The Nucleotide Sequence of the *lac* Operator," Proc. Nat. Acad. Sci. USA, Dec. 1973, vol. 70, No. 12, Part I, pp. 3581-3584.
Green et al., "Protective Groups in Organic Synthesis," copyright 1991, John Wiley & Sons, Inc., 12 pages.
Hung et al., "Samarium Diiodide Mediated Coupling of Glycosyl Phosphates with Carbon Radical or Anion Acceptors—Synthesis of C-Glycosides," Agnew. Chem. Int. Ed. Engl., 1996, vol. 35, No. 22, pp. 2671-2674.
International Search Report in Application No. PCT/EP2012/065547 mailed Nov. 28, 2012.
Jarreton et al., "Further Studies in 60 -C-Mannosylation Promoted by Samarium Diiodide," Tetrahedron Letters, 1997, vol. 38, No. 10, pp. 1767-1770.

(Continued)

*Primary Examiner* — Jennifer Dunston
*Assistant Examiner* — Addison D Ault
(74) *Attorney, Agent, or Firm* — Foley & Lardner LLP

(57) ABSTRACT

The present invention concerns compounds of the following formula (I) or a pharmaceutically acceptable salt thereof, a stereoisomer or a mixture of stereoisomers in any proportion, in particular a mixture of enantiomers, and particularly a racemate mixture, in which R represents H, OH or $OR^{19}$, as well as processes for preparing these compounds and their use as inducer for the transcription of genes under control of the lac promoter.

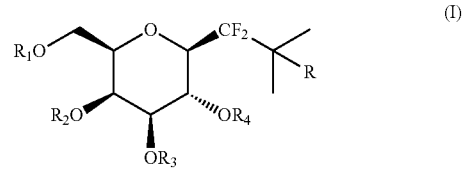

(I)

21 Claims, 4 Drawing Sheets

(56) References Cited

OTHER PUBLICATIONS

Ko et al., "Synthesis of Isobutyl-C-galactoside (IBCG) as in Isopropylthiogalactoside (IPTG) Substitute for Increased Induction of Protein Expression," Organic Letters, 2003, vol. 5, No. 10, pp. 1781-1783.

Kuzuhara et al., "Syntheses with Partially Benzylated Sugars. VIII. Substitution at C-5 in an Aldose. The Synthesis of 5-O-Methyl-D-glucofuranose Derivatives," Journal of Organic Chemistry, 1967, vol. 32, No. 8, pp. 2531-2534.

Lesimple et al. "Stereocontrolled Synthesis of C-Glycosides: Further Studies on the Organolithium Reagents Derived from 2-Deoxy-D-Glucose and 0-Glucose," Bioorganic & Medicinal Chemistry, 1994, vol. 2, No. 11, pp. 1319-1330.

Liu et al., "Multigram Synthesis of Isobutyl-β-C-galactoside as a Substitute of Isopropylthiogalactoside for Exogenous Gene Induction in Mammalian Cells," The Journal of Organic Chemistry, 2012, vol. 77, pp. 1539-1546.

Mazeas et al., "A Highly Stereoselective Synthesis of 1,2-trans-C-Glycosides via Glycosyl Samarium(III) Compounds," Agnew. Chem. Int. Ed. Engl., 1995, vol. 34, No. 8, pp. 909-912.

Menzella et al., "Novel *Escherichia coli* Strain Allows Efficient Recombinant Protein Production Using Lactose as Inducer," Biotechnology and Bioengineering, Jun. 2003, vol. 82, No. 7, pp. 809-817.

Miguel et al., "Synthesis of 1,2-trans C-glycosyl compounds by reductive samariation of glycosyl iodides," Chem. Comm., 2000, pp. 2347-2348.

Rajanikanth et al., "A Facile Synthesis of Nojirimycin," Tetrahedron Letters, vol. 30, No. 6, pp. 755-758.

Risseeuw et al., "Synthesis of alkylated sugar amino acids: conformationally restricted $_L$-Xaa-$_L$-Ser/Thr mimics," Organic & Biomolecular Chemistry, 2007, vol. 5, pp. 2311-2314.

Skrydstrup et al., "A General Approach to 1,2-trans-C-Glycosides via Glycosyl Samarium(III) Compounds," Chem. Eur. J., 1998, vol. 4., No. 4, pp. 655-671.

Urban et al., "Stereocontrolled Synthesis of α-C-Galactosamine Derivatives via Chelation-Controlled C-Glycosylation," J. Org. Chem., 1998, vol. 63, pp. 2507-2516.

Wittman et al., Stereoselective Synthesis of C-Glycosides with a Glycosyl Dianion, Angew. Chem. Int. Ed. Engl., 1993, vol. 32, No. 7, pp. 1091-1093.

GEM-DIFLUORINATED C-ISOPROPYLGALACTOSIDE DERIVATES

The present invention relates to gem difluorinated C-isopropylgalactoside derivates, the process for their preparation, and their use as inducers of recombinant protein production.

Allolactose, a disaccharide consisting of a β-galactose unit linked to a β-glucose unit, is the natural metabolite that triggers transcription of the inducible lac operon, only the galactose part being found necessary to block interaction between DNA and the repressor protein.

However, allolactose presents the disadvantage to be hydrolysable.

Amongst the non hydrolysable inducers, the well-known IPTG (isopropyl-β-D-thiogalactopyranoside) induces the transcription of the gene lacZ. IPTG binds to the repressor protein (product of the regulator gene lacI), preventing the repressor to bind the lac operator (lacO), and thus allowing RNA polymerase to transcribe genes. In cloning experiments, the gene lacZ is replaced by a gene coding for the protein of interest, so that this gene expression is under the control of the lacZ promoter, and more specifically under the control of the lac operator. Then the recombinant protein production is achieved by induction of gene transcription by inducers.

Nevertheless, if IPTG has a non hydrolysable structure, IPTG and its solution have to be stored at low temperature (−20° C.) to prevent their decomposition. It is necessary to prepare several IPTG samples to avoid freezing and defrost cycle, which could lead to IPTG deterioration. In traditional experiments, IPTG is added several times depending on the induction period because of its decomposition.

In order to develop stable and non hydrolysable inducers, an analog has already been prepared, such as IBCG (isobutyl-C-galactoside), in which the glycoside sulfur bond of the IPTG has been replaced by a methylene group (*Org. Lett.* 2003, 5, 1781; WO 2004/094445; *J. Org. Chem.* 2012, 77, 1539).

The substitution of the anomeric atom involved in the glycosidic bond by a $CH_2$ allows a better stability of the compound but a methylene group may also induce structural modification, which can affect its effectiveness.

The compounds of the present invention comprising a $CF_2$ group in the anomeric position represent molecular mimics of allolactose. They can thus induce the transcription of the gene lacZ or any other gene replacing the gene lacZ and coding for a recombinant protein of interest. Unlike allolactose, the compounds of the invention contain a $CF_2$ unit that creates a chemical bond, which is non-hydrolysable by the cell, preventing the cell from degrading the inducer; therefore its concentration remains constant overtime.

Indeed, the difluoromethylene $CF_2$ unit is a suitable group to mimic the oxygen of allolactose on an electronic and steric point of view. Intrinsic fluorine properties such as its small size, its high electronegativity, as well as the strength and the length of the C—F bond give all properties needed to replace the oxygen atom and to modulate biological properties while minimizing structural changes.

The presence of the two fluorine atoms onto the compounds of the invention gives thus a non-chemically and non-enzymatically hydrolysable structure and enhances the effectiveness of the galactosides with minimal structural modification. The gem-difluorinated C-galactosides insert also easily in the cell due to the hydrophilicity of the fluorine.

Moreover, unlike IPTG, these new galactoside derivates are stable at room temperature. The concentration of the galactosides of the invention is thus stable throughout the duration of the experiment.

The present invention proposes thus new inducers of the transcription of genes under control of the lac operator, which can be stored and transported in standard conditions without need of low temperature preservation, in order to overcome the drawbacks associated with the use of IPTG.

The present invention relates to compounds of the following formula (I)

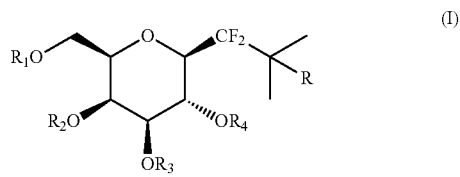

or a pharmaceutically acceptable salt thereof, a stereoisomer or a mixture of stereoisomers in any proportion, in particular a mixture of enantiomers, and particularly a racemate mixture, in which:
  R represents H, OH or $OR^{19}$,
  $R_1$ represents H, $R^5$, $C(O)R^5$, $P(O)(OR^6)(OR^7)$, $SiR^8R^9R^{10}$, or a O-protecting group such as a Bn or MOM group, and
  $R_2$, $R_3$ and $R_4$ represent, independently from one another, H, $R^{11}$, $C(O)R^{11}$, $siR^{12}R^{13}R^{14}$, or a O-protecting group such as a Bn or MOM group, or ($R_1$ and $R_2$) form together a chain —$CR^{15}R^{16}$— linking the oxygen atom carrying them,
  and/or ($R_3$ and $R_4$) or ($R_2$ and $R_3$) form a chain —$CR^{17}R^{18}$— linking the oxygen atom carrying them, with:
  $R^5$ and $R^{11}$ representing, independently of one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, aryl-$(C_1-C_6)$alkyl or $(C_1-C_6)$alkyl-aryl group, this group being optionally substituted with one or more groups chosen among a halogen atom, OH, COOH and CHO,
  $R^6$ and $R^7$ representing, independently of one another, a hydrogen atom or a $(C_1-C_6)$alkyl group,
  $R^8$ to $R^{10}$ and $R^{12}$ to $R^{14}$ representing, independently of each other, a $(C_1-C_6)$alkyl, aryl or aryl-$(C_1-C_6)$alkyl group,
  $R^{15}$ to $R^{18}$ representing, independently of each other, a hydrogen atom, or a $(C_1-C_6)$alkyl, aryl or aryl-$(C_1-C_6)$alkyl group,
  $R^{19}$ representing $COCOOR^{20}$, and
  $R^{20}$ representing a $(C_1-C_6)$alkyl group.

For the purpose of the invention, the term "pharmaceutically acceptable" is intended to mean what is useful to the preparation of a pharmaceutical composition, and what is generally safe and non toxic, for a pharmaceutical use.

The term "pharmaceutically acceptable salt" is intended to mean, in the framework of the present invention, a salt of a compound which is pharmaceutically acceptable, as defined above, and which possesses the pharmacological activity of the corresponding compound. Such salts comprise:

(1) hydrates and solvates, (2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Within the meaning of this invention, "stereoisomers" is intended to designate diastereoisomers and enantiomers. These are therefore optical isomers. Stereoisomers which are not mirror images of one another are thus designated as "diastereoisomers", and stereoisomers which are non-superimposable mirror images are designated as "enantiomers".

A carbon atom bond to four non-identical substituents is called a "chiral centre".

An equimolar mixture of two enantiomers is called a racemate mixture.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise ($C_1$-$C_6$)alkyl groups, such as methyl, ethyl tert-butyl; substituted methyl ethers, for example, methoxymethyl (MOM), benzyloxymethyl, 2-methoxyethoxymethyl, 2-(trimethylsilyl) ethoxymethyl, benzyl (Bn) and triphenylmethyl; tetrahydropyranyl ethers; substituted ethyl ethers, for example, 2,2,2-trichloroethyl; silyl ethers, for example, trimethylsilyl, t-butyldimethylsilyl (TBS) and t-butyldiphenylsilyl; and esters prepared by reacting the hydroxyl group with a carboxylic acid for example, acetate, propionate, benzoate and the like. It will be preferably a Bn or MOM group, and in particular a Bn group.

The term "halogen", as used in the present invention, refers to a fluorine, bromine, chlorine or iodine atom.

The term "($C_1$-$C_6$)alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "($C_2$-$C_6$)alkenyl", as used in the present invention, refers to a straight or branched unsaturated hydrocarbon chain containing from 2 to 6 carbon atoms and comprising at least one double bond including, but not limited to, ethenyl, propenyl, butenyl, pentenyl, hexenyl and the like.

The term "($C_2$-$C_6$)alkynyl", as used in the present invention, refers to a straight or branched unsaturated hydrocarbon chain containing from 2 to 6 carbon atoms and comprising at least one triple bond including, but not limited to, ethynyl, propynyl, butynyl, pentynyl, hexynyl and the like.

The term "($C_3$-$C_7$)cycloalkyl", as used in the present invention, refers to a hydrocarbon ring having 3 to 7 carbon atoms including, but not limited to, cyclopropyl, cyclopentyl, cyclohexyl and the like.

The term "5- to 7-membered heterocycloalkyl", as used in the present invention, refers to a saturated or unsaturated 5- to 7-membered cycle comprising one or more, advantageously 1 to 4, and preferably 1 or 2, heteroatoms chosen from among sulphur, nitrogen and oxygen atoms. It can be for example a pyrrolidinyl, piperidinyl, piperazinyl or morpholinyl group.

The term "aryl", as used in the present invention, refers to an aromatic group comprising preferably 5 to 10 carbon atoms and comprising one or more fused rings, such as, for example, a phenyl or naphtyl group. Advantageously, it will be a phenyl group.

The term "aryl-(C1-C6)alkyl", as used in the present invention, refers to an aryl group as defined above bound to the molecule via a (C1-C6)alkyl group as defined above. In particular, it will be a benzyl group.

The term "(C1-C6)alkyl-aryl", as used in the present invention, refers to a (C1-C6)alkyl group as defined above bound to the molecule via an aryl group as defined above. In particular, it will be a methylphenyl group, also called tolyl group.

The galactose moiety of the compounds of the invention can belong to the D and/or L series, and preferably to the D series.

According to a particular embodiment, R represents H or OH.

Advantageously, $R_1$ will represent H, $R^5$, $C(O)R^5$, $SiR^8R^9R^{10}$, or a O-protecting group such as a Bn or MOM group, and in particular H, $R^5$, or $C(O)R^5$, notably with $R^5$ representing a ($C_1$-$C_6$)alkyl, aryl, or aryl-($C_1$-$C_6$)alkyl group.

Preferably, $R_1$ will represent H or $R^5$, notably with $R^5$ representing a ($C_1$-$C_6$)alkyl, aryl, or aryl-($C_1$-$C_6$)alkyl group. More preferably, $R_1$=H.

Advantageously, $R_2$, $R_3$ and $R_4$ will represent, independently from one another, H, $R^{11}$, or $C(O)R^{11}$, an in particular H or $R^{11}$, notably with $R^{11}$ representing a ($C_1$-$C_6$)alkyl, aryl, or aryl-($C_1$-$C_6$)alkyl group. Preferably, $R_2$=$R_3$=$R_4$=H.

Preferably, $R_2$, $R_3$ and $R_4$ are identical and even more preferably, $R_1$, $R_2$, $R_3$ and $R_4$ are identical.

According to a particular advantageous embodiment, $R_1$=$R_2$=$R_3$=$R_4$=H, i.e. the compounds of the invention correspond to compounds of the following formula (Ia):

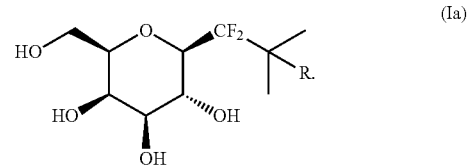

(Ia)

The compounds of the present invention can be chosen from the following compounds:

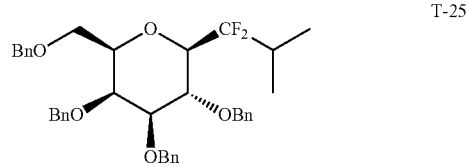

T-25

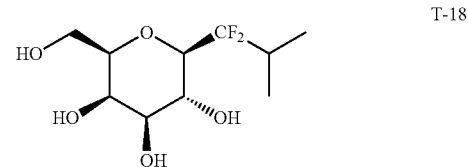

T-18

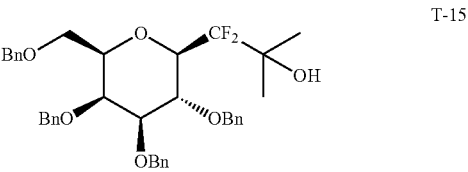

T-15

-continued

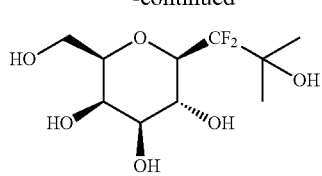
T-16

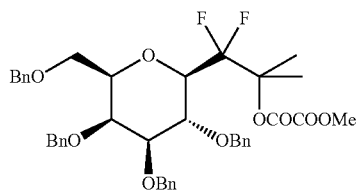
T-27

The present invention concerns also processes for the preparation of the compounds of formula (I).

The present invention concerns thus a process for preparing compounds of the present invention with R=H or OH, comprising the reaction of the ester function of a compound of the following formula (II):

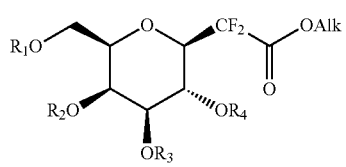
(II)

wherein $R_1$, $R_2$, $R_3$ and $R_4$ are as defined above and Alk represents a ($C_1$-$C_6$)alkyl group, with MeLi or MeMgHal, Hal representing a halogen atom such as a bromine or chlorine atom, and in particular a bromine atom.

This reaction can be carried out in conditions well known to the person skilled in the art, in particular in an ether as solvent, such as THF, and at a temperature comprised between −40° C. and room temperature, preferably between 0° C. and room temperature, and even more preferably at 0° C.

At least two molar equivalents of MeLi or MeMgHal relatively to the compound of formula (II) are needed.

Preferably, the reaction will be carried out with a compound of formula (II) wherein $R_1$, $R_2$, $R_3$ and $R_4$ do not represent a hydrogen atom, and advantageously represent a benzyl group. The compounds of formula (I) wherein $R_1$, $R_2$, $R_3$ and/or $R_4$ represent a hydrogen atom can be obtained by deprotecting in conditions well known to the person skilled in the art.

The compounds with R=$OR^{19}$ can be obtained from an additional step of substitution of R=OH in the presence of a compound of formula $R^{19}$Cl, i.e. $R^{20}$OC(O)C(O)Cl, for example methyloxalyl chloride when $R^{20}$=methyl, and DMAP (N,N-dimethylaminopyridine). Then, the compounds with R=H can be prepared from the compounds with R=$OR^{19}$ by a reduction, notably in the presence of $Bu_3SnH$ and AIBN (azobisisobutyronitrile).

The compounds of formula (II) can be prepared in 4 steps from galactose as described on schemes 1 and 2 below.

The resultant compounds of formula (I) can be separated from the reaction medium by methods well known to the person skilled in the art, such as by extraction, evaporation of the solvent or by precipitation or crystallisation (followed by filtration).

The same compounds of formula (I) can also be purified if necessary by methods well known to the person skilled in the art, such as by recrystallization, chromatography on a column of silica gel or high performance liquid chromatography (HPLC).

The present invention concerns also a first process for preparing compounds of the present invention with R=H, comprising the hydrogenation of the double bond of a compound of the following formula (III):

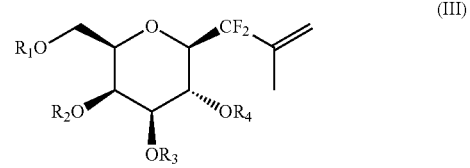
(III)

wherein $R_1$, $R_2$, $R_3$ and $R_4$ are as defined above.

This reaction can be carried out in conditions of hydrogenation well known to the person skilled in the art. The reaction can be carried out under a hydrogen atmosphere in the presence of a hydrogenation catalyst such as Pd/C, notably in the presence of an acid such as HCl.

Preferably, the reaction will be carried out with a compound of formula (III) wherein $R_1$, $R_2$, $R_3$ and $R_4$ do not represent a hydrogen atom, and advantageously represent a benzyl group. The compounds of formula (I) wherein $R_1$, $R_2$, $R_3$ and/or $R_4$ represent a hydrogen atom can be obtain by a deprotecting step in conditions well known to the person skilled in the art. When $R_1$, $R_2$, $R_3$ and $R_4$ represent a benzyl group, both deprotection and reduction of the double bound can be jointly conducted, under a hydrogen atmosphere in the presence of a hydrogenation catalyst such as Pd/C, notably in the presence of an acid such as HCl.

The compounds of formula (III) can be prepared by dehydration of a compound of formula (I) wherein R represents an OH. The dehydration can be carried out in the presence of $POCl_3$ in pyridine as solvent, notably at a temperature comprised between 40° C. and 80° C.

The compounds of formula (II) can be prepared in 4 steps from galactose as described on schemes 1 and 2 below.

The obtained compound of formula (I) can be separated from the reaction medium by methods well known to the person skilled in the art, such as by extraction, evaporation of the solvent or by precipitation or crystallisation (followed by filtration).

The obtained compound of formula (I) can then be purified if necessary by methods well known to the person skilled in the art, such as by recrystallization, distillation, chromatography on a column of silica gel or high performance liquid chromatography (HPLC).

The present invention concerns also a second process for preparing compounds of the present invention with R=H, comprising the fluorination of the keto function of a compound of the following formula (IV):

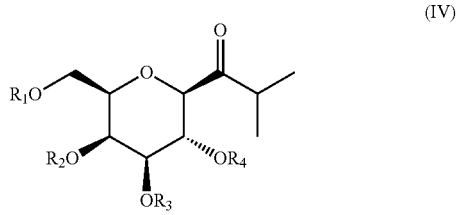
(IV)

wherein $R_1$, $R_2$, $R_3$ and $R_4$ are as defined above.

The fluorination can be carried out in conditions well known to the person skilled in the art in the presence of a fluorinating agent, such as diethylaminosulfur trifluoride (DAST), HF-pyridine or deoxo-fluor, and preferably with DAST.

Preferably, the fluorination will be carried out with a compound of formula (IV) wherein $R_1$, $R_2$, $R_3$ and $R_4$ do not represent a hydrogen atom, and advantageously represent a benzyl group. The compounds of formula (I) wherein $R_1$, $R_2$, $R_3$ and/or $R_4$ represent a hydrogen atom can be obtain by a deprotecting step in conditions well known to the person skilled in the art.

The compounds of formula (IV) can be prepared by oxidation of the corresponding alcohol (see schemes 3 and 4 below).

The resultant compounds of formula (I) can be separated from the reaction medium by methods well known to the person skilled in the art, such as by extraction, evaporation of the solvent or by precipitation or crystallisation (followed by filtration).

The same compounds of formula (I) can also be purified if necessary by methods well known to the person skilled in the art, such as by recrystallization, chromatography on a column of silica gel or high performance liquid chromatography (HPLC).

A process to prepare compounds of formula (I) with R=H, OH or $OR^{19}$ is illustrated on the scheme 1 below:

presence of molecular sieves and acetic acid; 4-methylmorpholine N-oxide (NMO) in the presence of tetra-n-propylammonium tetra-oxoruthenate (VII) (also called tetra-n-propylammonium per-ruthenate—TPAP) as described in *Carbohydrate Research* 1994, 260(2), 243-250; or $Pd(OAc)_2$ and $PPh_3$ as described in *Carbohydrate Research* 2004, 339 (7), 1377-1380, and leads to the lactone T-2.

The lactone T-2 is then transformed into the difluoroester T-3 notably through a Reformatsky reaction using $BrCF_2CO_2Et$ with Zinc in THF under reflux (WO 2004/014928) or with Zinc and a metal promoter such as $CeCl_3$ or $Cp_2TiCl_2$ in THF at room temperature; or using $SmI_2$ in THF, such as described in *Synlett* 2005, 17, 2627-2630.

The hydroxyl in anomeric position is removed through a two steps process, with first a substitution of the hydroxyl by a halogen such as bromine or chlorine using $SOBr_2$ or $SOCl_2$ and pyridine to lead to T-4, followed by the use of tributyltin (Org. Lett. 2002, 4(5), 757-759; WO 2007/125194 and WO 2007/125203) or tris(trimethylsilyl)silane (TTMSS)/azobisisobutyronitrile (AIBN) in toluene to give the ester T-5.

Then, the addition of an organometallic reagent, such as methyllithium or methylmagnesium bromide, onto the ester moiety of T-5, gives the compound T-6. Compound T-6 can then be deprotected using classical reaction to lead to compound T-7.

Compound T-6 can also be dehydrated under dehydration conditions, such as in the presence of $POCl_3$ in pyridine, to Scheme 1

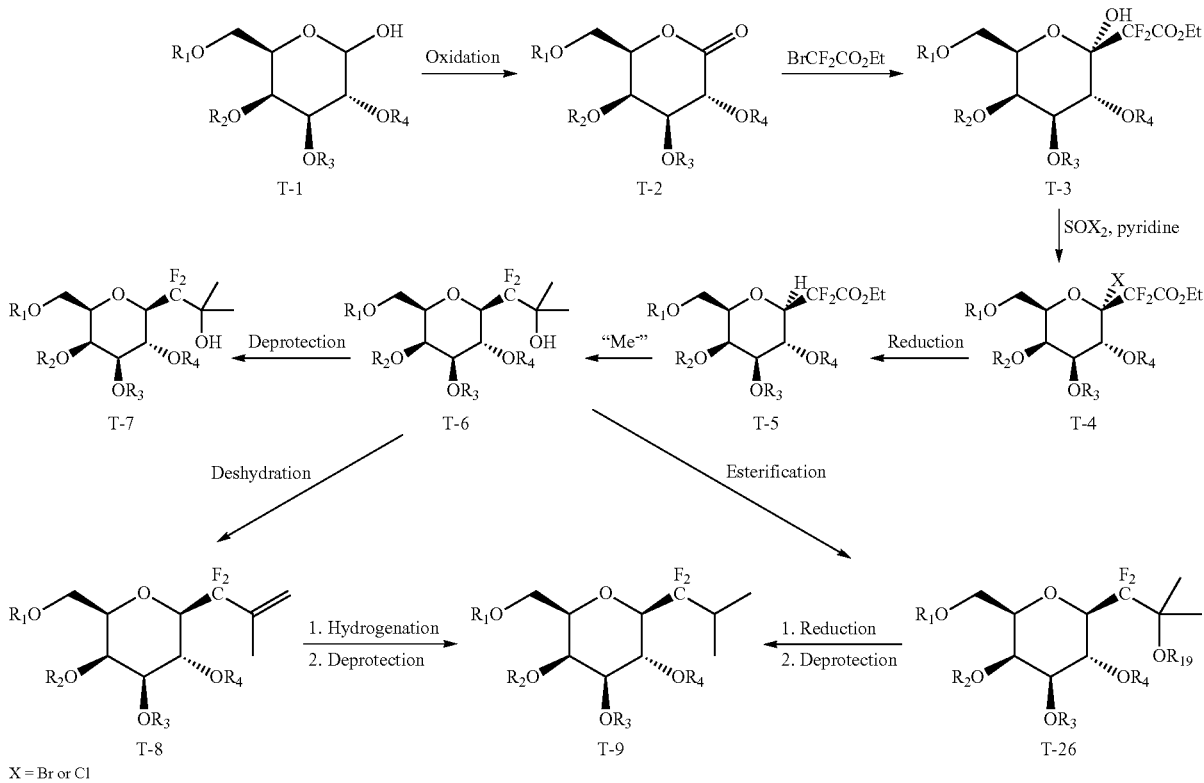

X = Br or Cl

The lactol T-1 is oxidized through well known processes such as a modified Swern approach using dimethyl sulfoxide (DMSO) and $Ac_2O$ as described in *Tetrahedron Letters* 1989, 30(6), 755-758 or *Journal of Organic Chemistry* 1967, 32(8), 2531-2534; dimethyl sulfoxide activated by oxalyl chloride with a base such as $Et_3N$; pyridinium dichromate (PDC) in the give compound T-8. Hydrogenation of the double bond is then performed followed by the appropriate deprotecting step to give compound T-9.

According to another approach compound T-6 can be esterified with $R^{19}Cl$ such as methyloxalyl chloride and DMAP to lead to compound T-26. Reduction with tributyltin hydride in the presence of an initiator such as AIBN followed by the appropriate deprotecting step afford compound T-9.

This process has been applied to the preparation of inducers T-16 and T-18 as illustrated on scheme 2 below:

lowed by a reduction step with tributyltin hydride and AIBN in toluene and a hydrogenation.

Another process to prepare compounds of formula (I) with R=H is illustrated on the scheme 3 below:

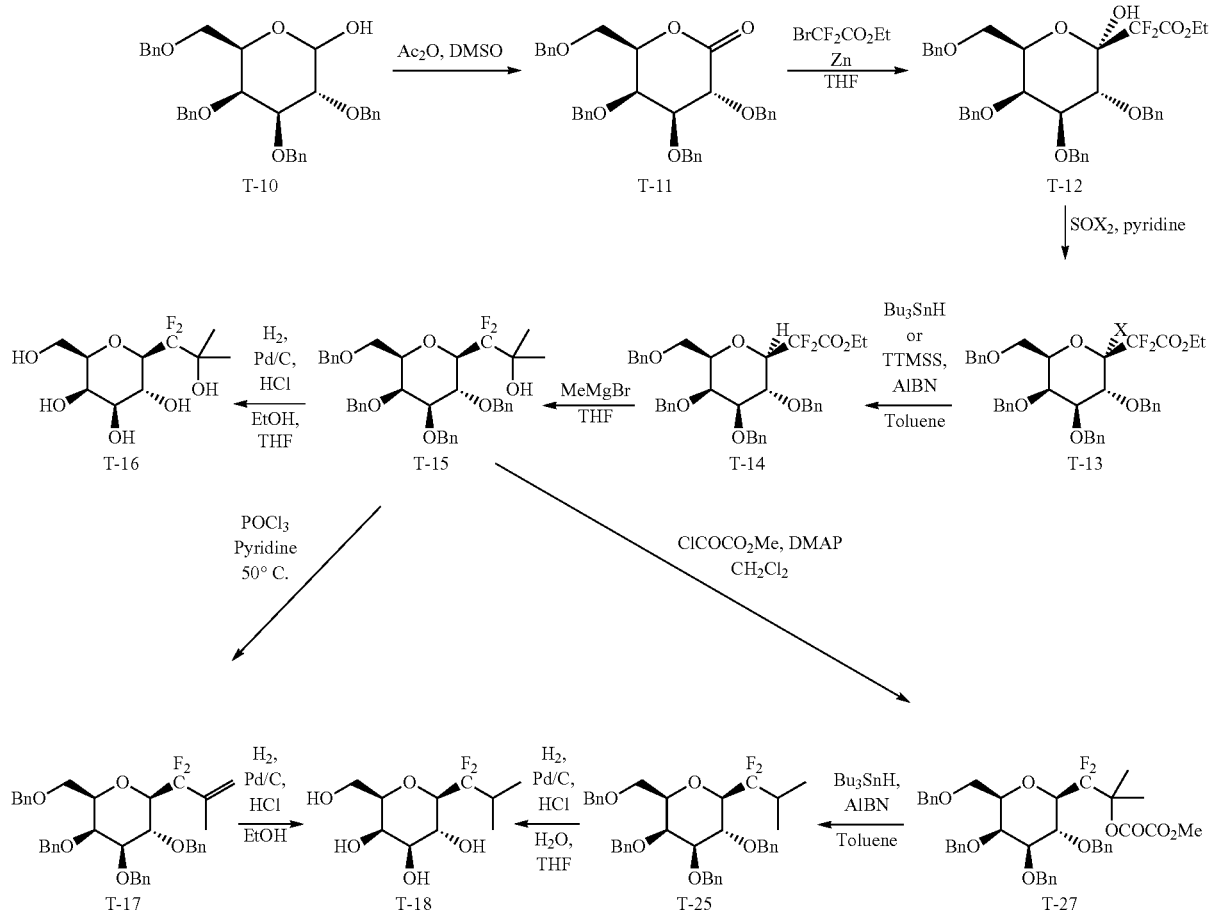

X = Br or Cl

The first step is an oxidation of the commercially available compound T-10 to give the lactone T-11 using acetic anhydride and DMSO. Then, the introduction of the difluoroester moiety through a Reformatsky reaction using Zinc in THF under reflux leads to compound T-12. The compound T-14 can then be prepared by reaction of compound T-12 with thionyl bromide or thionyl chloride and pyridine to give the brominated or chlorinated compound T-13, followed by a reduction with tributyltin hydride or TTMSS/AIBN in toluene. The addition of an organometallic reagent (such as methyllithium or methylmagnesium bromide) onto the ester moiety of T-14 gives compound T-15. The difluorinated compound T-15 can be debenzylated to give compound T-16 as an inducer.

Another inducer T-18 is obtained through the dehydration of the alcohol intermediate T-15 under POCl₃/pyridine conditions, followed by hydrogenation of the T-17 compound thus obtained.

Inducer T-18 is also obtained from an esterification of the compound T-15 with methyloxalyl chloride and DMAP, fol-

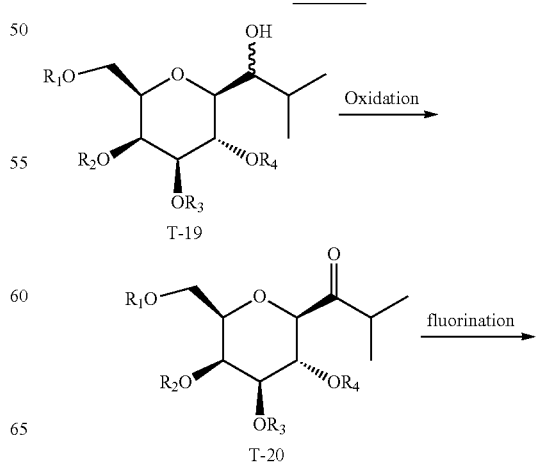

-continued

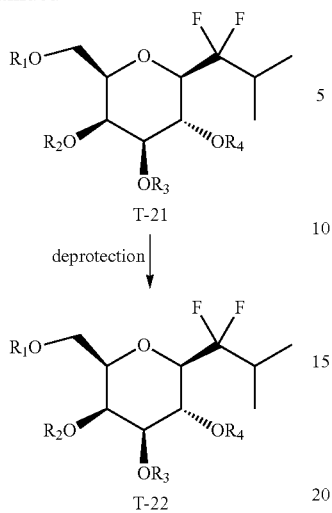

T-21 deprotection ↓

T-22

T-19 is oxidized into T-20 under usual condition as pyridinium chlorochromate (PCC). However other oxidizing agents can also be used, such as TEMPO ((2,2,6,6-tetramethylpiperidin-1-yl)oxyl), Dess-Martin periodinane, and the like. The ketone T-20 is then fluorinated to lead to compound T-21, notably with diethylaminosulfur trifluoride (DAST). Other fluorinating reagents can also be used such as HF-pyridine or Deoxo-Fluor. T-21 is then deprotected to lead to T-22.

Compounds T-19 can be obtained from different starting material with various synthetic pathways as described in literature such as *Chem. Commun.* 2000, 2347; *J. Org. Chem.* 1998, 63, 2507; *Org. Biomol. Chem.* 2007, 5, 2311; *Angew. Chem. Int. Ed. Eng.* 1993, 32, 1091; *J. Org. Chem.* 2001, 66, 1768; *Tetrahedron Lett.* 1998, 39, 7699; *Angew. Chem. Int. Ed.* 2002, 41, 3242; *Bioorganic & Medicinal Chemistry* 1994, 2(11), 1319; Helv. Chim. Acta 1994, 77, 2060; *Angew. Chem. Int. Ed. Eng.* 1996, 35, 2671; *Angew. Chem. Int. Ed. Eng.* 1995, 34, 909; *Chem. Eur. J.* 1998, 4, 655; *Tetrahedron Letters* 1997, 38, 1767.

This process has been applied to the preparation of inducer T-18 as illustrated on scheme 4 below:

Scheme 4

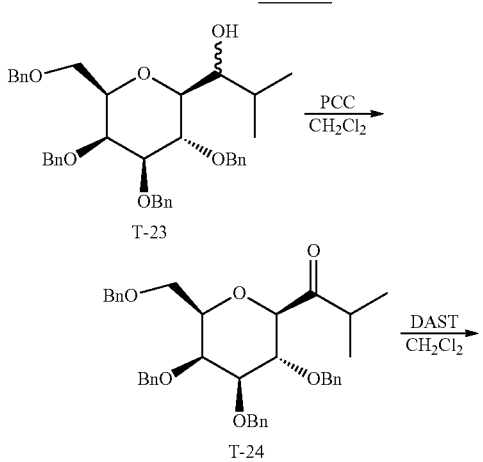

-continued

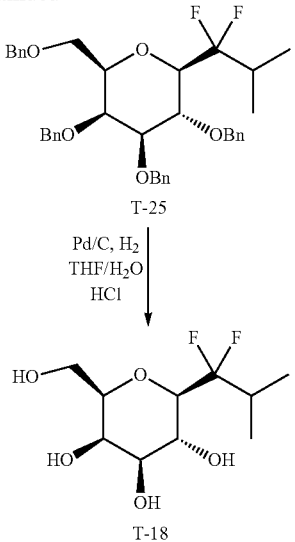

T-25

Pd/C, H₂
THF/H₂O
HCl ↓

T-18

The ketone T-24 is obtained through oxidation of the compound T-23, under usual condition, such as pyridinium chlorochromate (PCC). The synthesis of the difluorinated compound T-25 is achieved with standard fluorinating agent, such as diethylaminosulfur trifluoride (DAST). The compound T-18 is then obtained through a deprotecting step such as hydrogenation in the present case where the protecting groups are benzyl groups.

The present invention also relates to the use of compounds of formula (Ia) as inducers for the transcription of a gene under control of a promoter comprising at least one operator sequence capable of binding the lac repressor.

In particular, the present invention provides a method for producing a protein comprising the following successive steps:
 a) transforming a host cell with a vector comprising a gene encoding said protein and a promoter, said promoter comprising at least one operator sequence capable of binding the LacI repressor, and
 b) growing the transformed cell of step a) in the presence of a compound of formula (Ia).

The term "host cell", as used herein, is intended to refer to a cell into which a recombinant expression vector has been introduced in order to express recombinant proteins. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

More specifically, a host cell according to the invention is a cell in which binding between the lac repressor and an operator sequence is capable of preventing transcription initiation. The host cell can be a bacterium such as *Escherichia coli* (*E. coli*).

The term "vector", as used herein, is intended to refer to a nucleic acid molecule capable of transporting another nucleic acid to which it has been linked. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Various vectors are publicly available, for cloning (amplification of the DNA) or for expression. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art (see, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al., eds., 1998, Current Protocols in Molecular Biology, John Wiley & Sons, NY).

Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

In order to express the recombinant proteins of the invention, the polynucleotides encoding said proteins are inserted into expression vectors such that the genes are operatively linked to transcriptional and translational sequences. Expression vectors include plasmids, YACs, cosmids, retrovirus, adenovirus, EBV-derived episomes, and all the other vectors that the skilled man will know to be convenient for ensuring the expression of the protein of interest.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

"Promoter" or "operator" as used herein may mean a synthetic or naturally-derived molecule which is capable of conferring, activating or enhancing expression of a nucleic acid in a cell. A promoter may comprise one or more specific transcriptional regulatory sequences to further enhance expression or to alter the spatial expression or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

The promoter can be natural or artificial.

A preferred promoter according to the invention contains operator sequences capable of binding the LacI repressor protein. The "LacI repressor protein" (or "LacI repressor" or "LacI": for the purpose of this application, these terms are synonymous) according to the invention is a protein which is capable of inhibiting the transcription of the *E. coli* lacZ operon though physical interaction with a sequence within the lacZ promoter. More preferably, the "LacI repressor protein" according to the invention is a protein having the sequence of accession number NP_414879.

In one embodiment, the operator sequence capable of binding the LacI repressor protein has the sequence sharing at least 60%, preferably at least 75%, more preferably at least 85%, still more preferably at least 95% and even more preferably at least 99% identity with the sequence displayed in SEQ ID NO. 1: TGGAATTGTGAGCGG ATAACAATT. A preferred operator sequence capable of binding the LacI repressor protein is the lac operator. The lac operator is described in e.g. Gilbert & Maxam, (*Proc. Natl. Acad. Sci. U.S.A.*, 70(12): 3581-3584, 1973). In a further preferred embodiment, the lac operator has the sequence of SEQ ID NO. 1.

In another embodiment, the method of the invention comprises, after step b), an additional step:

c) To isolate the protein from the transformed cell.

The protein can be isolated using methods known to those skilled in the art. For example, the protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification.

Alternatively, a cation exchange step can be employed. Suitable cation exchangers include various insoluble matrices comprising sulfopropyl or carboxymethyl groups. Sulfopropyl groups are preferred (e.g., S-Sepharose B columns). The purification of the protein from culture supernatant may also include one or more column steps over such affinity resins as concanavalin A-agarose, heparin-Toyopearl or Cibacrom blue 3GA Sepharose B; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the protein of the invention.

Affinity columns including antibodies to the protein of the invention can also be used in purification in accordance with known methods. Some or all of the foregoing purification steps, in various combinations or with other known methods, can also be employed to provide a substantially purified isolated recombinant protein. Preferably, the isolated protein of the invention is purified so that it is substantially free of other proteins.

FIGURES

EXAMPLES

Figure 1:
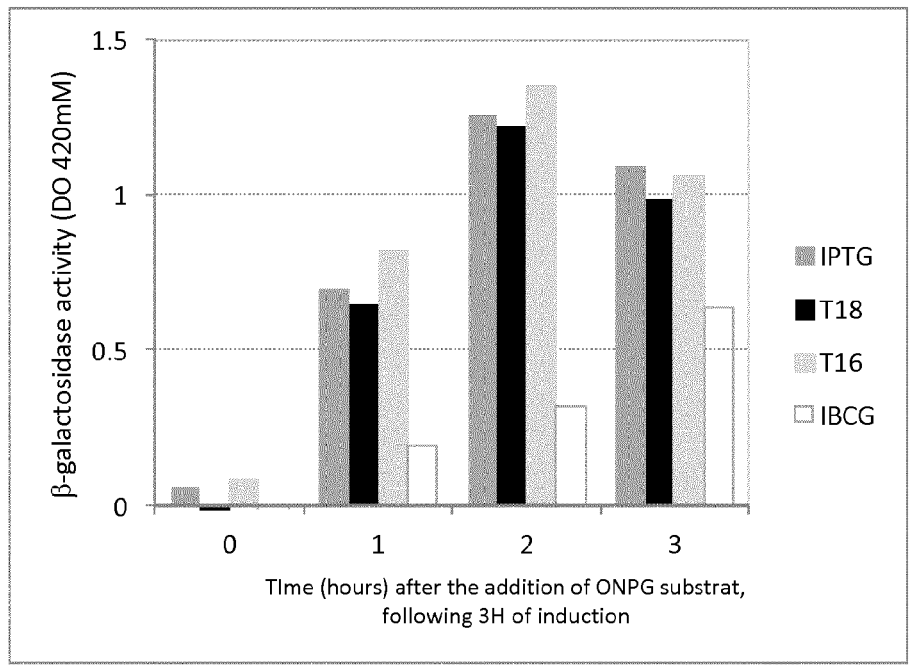
FIG. 1 represents the β-galactosidase expression induced by compounds T-16, T-18, IPTG and IBCG at a concentration of 0.5 mM.

I—Synthesis of the Compounds of the Invention

The features of the devices used to conduct analyses of all of the compounds described in this application are indicated hereinbelow.

The $^{19}$F NMR spectra were recorded on BRUKER DPX 300 spectrometer. The internal reference used was fluorotrichloromethane $CFCl_3$. Chemical shifts are expressed in parts per million (ppm), and coupling constants (J) in Hertz (Hz).

The following abbreviations were used:

s for singlet, bs for a broad singlet, d for doublet, t for triplet, qdt for quartet, m for multiplet or massive, dd for doublet of doublets, etc.

The mass spectra were obtained on a spectrophotometer of the Micromass TOF-SPEC E 20 kV, α-cyano type, for MALDI ionization and JEOL AX500, 3 kV, Canon FAB JEOL, Xe, 4 kV, 10 μA limiting current, Gly-NBA 50:50 for FAB ionization and on Waters LCT Premier XE coupled to a LC Waters Acquity.

Separations via column chromatography were carried out under light pressure by following chromatography techniques on Kieselgel 60 silica (230-400 Mesh, Merck) and Automated column chromatography was performed on Biotage SP4 instruments using Biotage® SNAP cartridges. Follow-up is ensured via thin-layer chromatography (TLC) with Kieselgel 60F-254-0.25-mm plates. The ratio of the migration distance of a compound on a given support to the migration distance of an eluent is called the retardation factor (Rf).

Exemplary compound preparations according to the invention will be described hereinbelow, for non-limiting, illustrative purposes.

Synthesis of Compound T-12

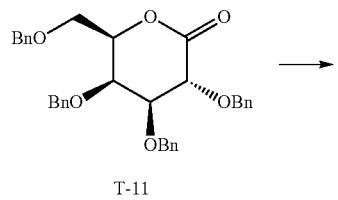

T-11

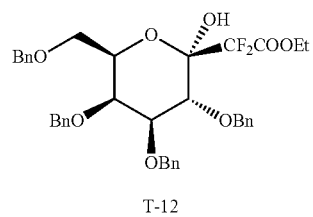

T-12

In a round bottom flask containing zinc Zn (previously activated) (17.6 g; 269 mmol; 7 eq.) in THF (250 mL) under a reflux, a solution of compound T-11 (20.3 g; 37.7 mmol; 1 eq.) and ethyl bromodifluoroacetate (14.5 mL; 113 mmol; 3 eq.) in THF (250 mL) was added dropwise. The reaction was heated under reflux for 3 hours. At the end of the reaction, the zinc was filtered and a solution of 1N HCl was added. The mixture was extracted with ethyl acetate, dried over magnesium sulfate and evaporated. The crude residue was purified on a chromatography column (cyclohexane/ethyl acetate 98/02 to 80/20) to give compound T-12 (20.4 g; 30.8 mmol) in the form of a white powder with a yield of 82%.

Rf: 0,35 (cyclohexane/ethyl acetate 80/20).

$^{19}$F NMR ($CDCl_3$; 282,5 MHz): −118.4 (1F, d, J=256 Hz); −120.2 (1F, d, J=256 Hz).

Mass (ESI$^+$): 685.7[M+Na]$^+$; 701.5[M+K]$^+$.

Synthesis of Compound T-13 with X═Br

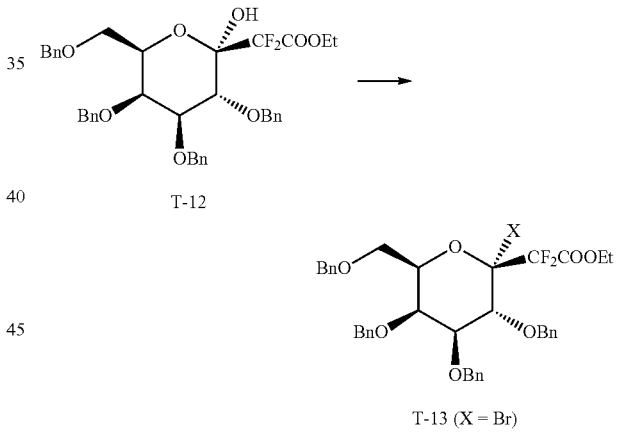

T-12

T-13 (X = Br)

To a solution of compound T-12 (21 g; 31.7 mmol) in $CH_2Cl_2$ (250 mL) at −30° C., $SOBr_2$ (3.7 mL; 47.6 mmol; 1.5 eq.) was added slowly. After 30 minutes, pyridine was added (3.8 mL; 47.6 mmol; 1.5 eq.) and the solution was stirred for additional 30 minutes at −30° C. Then, the solution was quenched with a 2N aqueous solution of HCl, extracted with $CH_2Cl_2$ and the combined organic layers were dried over magnesium sulfate and evaporated. The compound T-13 (X═Br) was obtained without purification in the form of a yellow powder with a quantitative yield.

Rf: 0,54 (cyclohexane/ethyl acetate 80/20).

$^{19}$F NMR ($CDCl_3$; 282,5 MHz): −107.5 (1F, d, J=249 Hz); −111.9 (1F, d, J=249 Hz).

Mass (ESI$^+$): 742.20[M+$H_2O$]$^+$; 763.13 [M+K]$^+$.

Synthesis of Compound T-13 with X=Cl

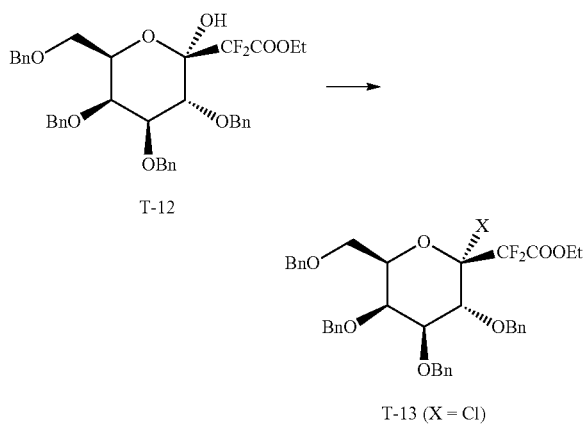

Compound T-13 (X=Cl) was obtained in the form of a colorless oil with a yield of 73%, by following the same procedure as above, replacing SOBr$_2$ with SOCl$_2$.

$^{19}$F NMR (CDCl$_3$; 282,5 MHz): −112.00 (1F, d, J=250 Hz); −114.12 (1F, d, J=250 Hz).

Mass (MALDI$^+$): 703 [M+Na]$^+$; 719[M+K]$^+$.

Synthesis of Compound T-14

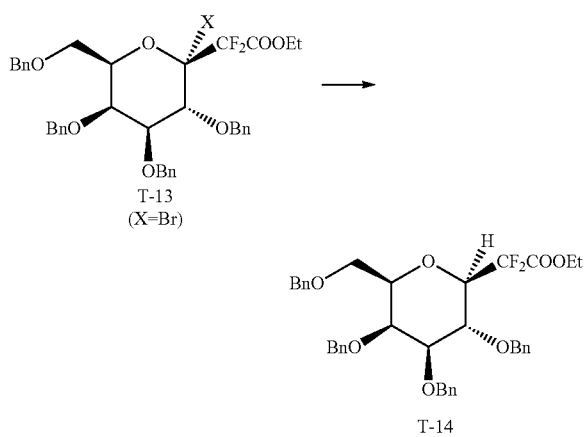

Process 1:

Under inert atmosphere, tributylstannane Bu$_3$SnH (0.5 mL; 1.86 mmol) was added slowly to a solution of compound T-13 (X=Br) (0.88 g; 1.21 mmol) in toluene (26 mL) and the mixture was heated at reflux and stirred for 1 hour. At the end of the reaction, the solution was concentrated and the crude residue was purified on a chromatography column (cyclohexane/ethyl acetate 100/0 to 90/10) to give compound T-14 (0.58 g; 0.90 mmol) in the form of a colorless oil with a yield of 74%.

Process 2:

Under an inert atmosphere, AIBN (113 mg, 0.69 mmol, 1 eq) and TTMSS (Tris(trimethylsilyl)silane) (0.42 mL, 1.36 mmol, 2 eq) were added to a solution of compound T-13 (X=Br) (497 mg; 0.69 mmol) in toluene (14 mL) and the resultant mixture was heated to 90° C. for 5 hours. The solution was then concentrated and the crude residue was purified by chromatography (cyclohexane/ethyl acetate 100/0 to 80/20) to give compound T-14 (279 mg, 63% yield) as colorless oil.

$^{19}$F NMR (CDCl$_3$; 282,5 MHz): −116.3 (1F, dd, J=259 Hz, J=13 Hz); −117.8 (1F, dd, J=259 Hz, J=9 Hz).

Mass (ESI$^+$): 647.33[M+H]$^+$; 669.4[M+Na]$^+$.

Synthesis of Compound T-15

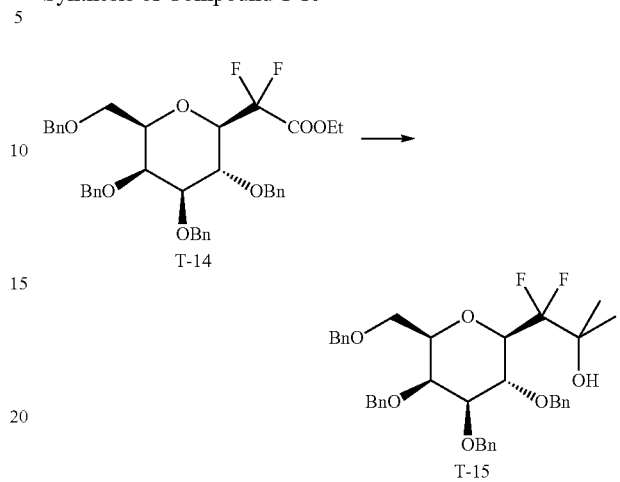

To a solution of compound T-14 (307 mg; 0.47 mmol; 1 eq.) in THF (4.7 mL) cooled to −20° C. was added dropwise under an inert atmosphere a solution of methyl magnesium bromide in THF (1 M; 1.42 mL; 1.42 mmol; 3 eq.). After stirring at −20° C. for 5 minutes the solution was warmed to 0° C. and stirred for 1 hour. Then a saturated aqueous solution of NH$_4$Cl was added and the reaction medium was extracted with diethyl ether. The combined organic phases were dried over MgSO$_4$, filtered and evaporated. The residue was purified on a chromatography column (cyclohexane/ethyl acetate 95/5 to 60/40) in order to produce compound T-15 (228 mg; 0.36 mmol) in the form of a yellow oil with a yield of 77%.

Rf: 0.50 (cyclohexane/ethyl acetate 70/30).

$^{19}$F NMR (CDCl$_3$, 282.5 MHz): −110.9 (1F, d, J=260 Hz); −126.4 (1F, dd, J=260 Hz, J=20 Hz).

Mass (ESI$^+$): 633.5[M+H]$^+$; 650.6[M+H$_2$O]$^+$; 655.6[M+Na]$^+$; 671.6[M+K]$^+$.

Synthesis of Compound T-16

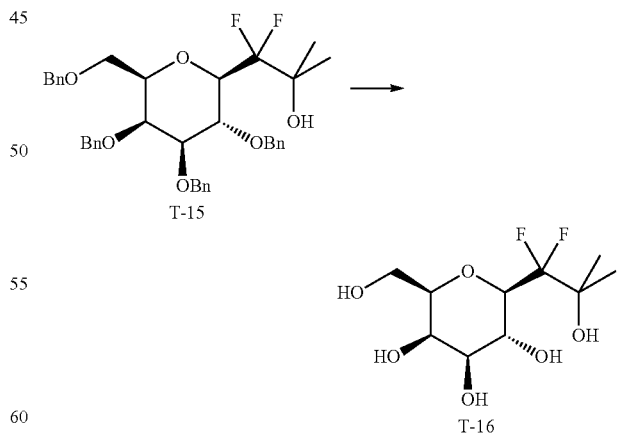

In a round bottom flask compound T-15 (414 mg; 0.65 mmol) was dissolved in a mixture of ethanol (0.3 mL), tetrahydrofuran (5.6 mL) and concentrated HCl (1 to 2 drops) in the presence of Pd/C, under a hydrogen atmosphere. The reaction medium was stirred for 24 h, then Millipore-filtered, evaporated and lyophylized in order to give compound T-16 (171 mg; 0.63 mmol) in the form of a white solid with a quantitative yield.

Rf: 0.31 (dichloromethane/methanol 80/20).

$^{19}$F NMR (CD$_3$OD, 282.5 MHz): −115.8 (1F, dd, J=263 Hz; J=9 Hz); −121.5 (1F, dd, J=263 Hz, J=16 Hz).

Mass (ESI$^+$): 295.1 [M+Na]$^+$; 311.1 [M+K]$^+$.

Synthesis of Compound T-17

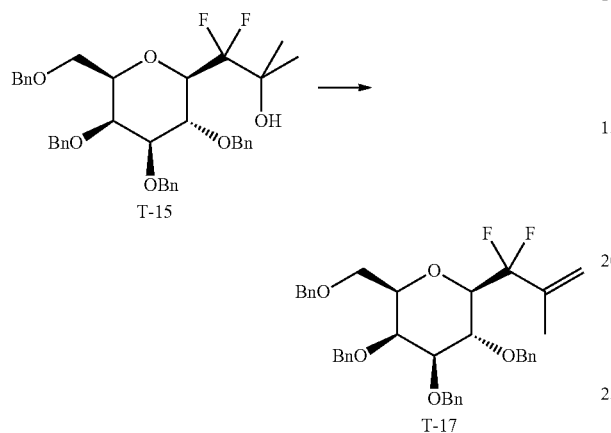

In a round bottom flask compound T-15 (424 mg; 0.67 mmol) was dissolved in pyridine (1.3 mL) and at 0° C. POCl$_3$ (313 µL; 3.36 mmol; 5 eq.) was added dropwise. The solution was warmed to room temperature and then heated to 50° C. for 15 hours. At the end of the reaction, the mixture was diluted with diethyl ether before a 1N HCl aqueous solution was then added. The layers were separated and the aqueous phase was extracted with diethyl ether. The combined organic phases were washed with brine, dried over MgSO$_4$, filtered and evaporated to give compound T-17 in the form of colorless oil with a yield of 96%.

$^{19}$F NMR (CDCl$_3$, 282.5 MHz): −104.8 (1F, dd, J=252 Hz; J=7 Hz); −112.7 (1F, dd, J=252 Hz, J=14 Hz).

Mass (ESI$^+$): 637.3[M+Na]$^+$; 653.28[M+K]$^+$.

Synthesis of Compound T-27

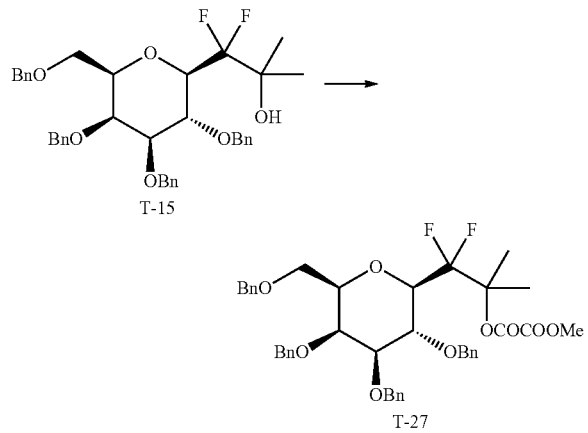

To a solution of compound T-15 (126 mg; 0.2 mmol) in CH$_2$Cl$_2$ (1.9 mL) was added 4-dimethylaminopropylamine (DMAP, 110 mg, 0.9 mmol; 4.5 eq.) and methyloxalyl chloride (0.09 mL; 1 mmol; 5 eq.). The mixture was stirred at room temperature for 45 min., poured into water and extracted with CH$_2$Cl$_2$. The combined organic layers were dried over Na$_2$SO$_4$, filtered and evaporated. The compound T-27 (118 mg) was involved in the next step without purification.

$^{19}$F NMR (CDCl$_3$; 282,5 MHz): −113.1 (1F, d, J=264 Hz); −122.9 (1F, dd, J=264 Hz, J=20 Hz).

Mass (ESI$^+$): 719.3 [M+H]$^+$; 736.3 [M+NH$_4$]$^+$; 741.3 [M+Na]$^+$; 757.3 [M+K]$^+$.

Synthesis of Compound T-24

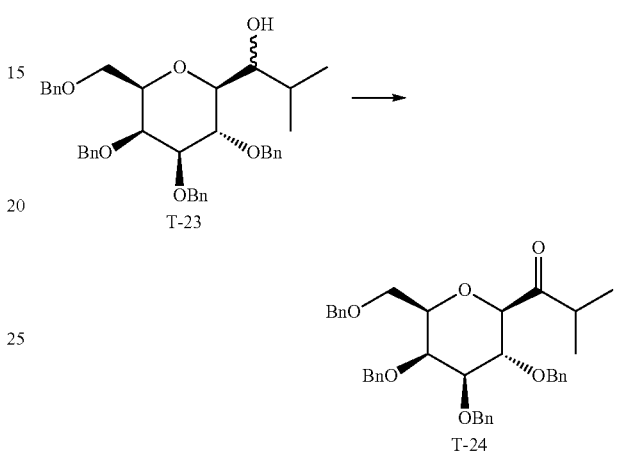

To a solution of compound T-23 (which can be obtained from different starting material with various synthetic pathways as described in literature such as *Chem. Commun.* 2000, 2347; *J. Org. Chem.* 1998, 63, 2507; *Org. Biomol. Chem.* 2007, 5, 2311; *Angew. Chem. Int. Ed. Eng.* 1993, 32, 1091; *J. Org. Chem.* 2001, 66, 1768; *Tetrahedron Lett.* 1998, 39, 7699; *Angew. Chem. Int. Ed.* 2002, 41, 3242; *Bioorganic & Medicinal Chemistry* 1994, 2(11), 1319; *Helv. Chim. Acta* 1994, 77, 2060; *Angew. Chem. Int. Ed. Eng.* 1996, 35, 2671; *Angew. Chem. Int. Ed. Eng.* 1995, 34, 909; *Chem. Eur. J.* 1998, 4, 655; *Tetrahedron Letters* 1997, 38, 1767). (400 mg; 0.67 mmol; 1 eq.) in dichloromethane (20 mL) was added PCC (578 mg; 2.68 mmol; 4 eq.). The mixture was stirred for 12 hours at room temperature, then the reaction medium was filtered through Celite, washed with water, extracted with dichloromethane, dried over MgSO$_4$ and concentrated. The crude residue was purified on a chromatography column (cyclohexane/ethyl acetate 95/05 to 60/40) to yield compound T-24 (200 mg; 0.34 mmol; 51%) in the form of a white powder.

Rf: 0.42 (cyclohexane/ethyl acetate 80/20).

Mass (ESI$^+$): 595.47[M+H]$^+$; 612.60[M+H$_2$O]$^+$.

Synthesis of Compound T-25

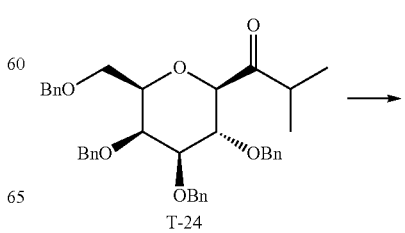

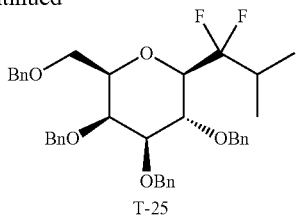

Process 1:

Diethylaminosulfur trifluoride DAST (559 µL; 4.54 mmol; 15 eq.) was added under an inert atmosphere to compound T-24 (181 mg; 0.30 mmol; 1 eq.) and the reaction medium was stirred overnight at 70° C. At 0° C. the solution was diluted with dichloromethane and solid NaHCO₃, water and ice were carefully added. The mixture was stirred for 30 min, and then extracted with dichloromethane, washed with brine, dried over magnesium sulfate and evaporated. The crude residue was purified on a chromatography column (cyclohexane/ethyl acetate 90/10 to 80/20) in order to produce compound T-25 (66 mg; 0.11 mmol) in the form of an orange oil with a yield of 37%.

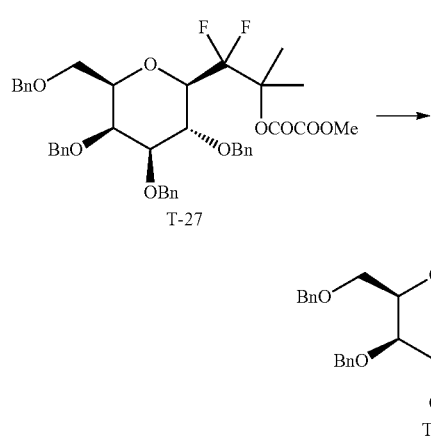

Process 2:

Bu₃SnH (0.09 mL; 0.3 mmol) was added to a solution of compound T-27 (118 mg) and AIBN (24 mg, 0.15 mmol) in toluene (3.2 mL). The mixture was stirred 1 h at 100° C. Then, the solvent was evaporated and the crude mixture was purified by silica gel chromatography (cyclohexane/ethyl acetate 98/02 to 80/20) to afford compound T-25 (40 mg, 0.07 mmol).

Rf: 0.25 (cyclohexane/ethyl acetate 90/10).

$^{19}$F NMR (CDCl₃, 282.5 MHz): −112.4 (1F; ddd; J=252 Hz; J=20 Hz; J=5 Hz); −120.8 (1F; ddd; J=252 Hz; J=26 Hz; J=4 Hz).

Mass (ESI⁺): 617.27[M+H]⁺; 634.27[M+H₂O]⁺.

Synthesis of Compound T-18

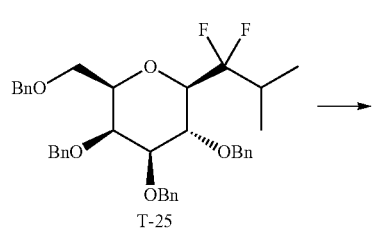

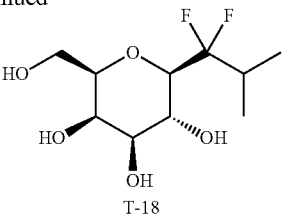

Process 1:

In a round bottom flask compound T-25 (69 mg; 0.11 mmol) was dissolved in a mixture of water, tetrahydrofuran and 0.1N HCl in the presence of Pd/C, under a hydrogen atmosphere. The reaction medium was stirred for 24 h, then Millipore-filtered and evaporated in order to give compound T-18 (29 mg; 0.11 mmol) in the form of a white solid with a quantitative yield.

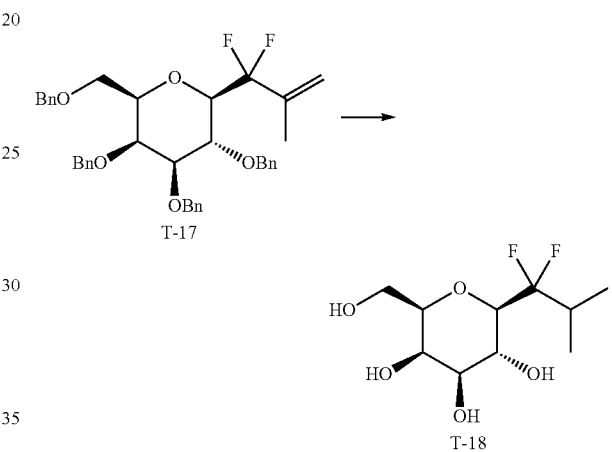

Process 2:

In a round bottom flask compound T-17 (160 mg; 0.26 mmol) was dissolved in a mixture of EtOH (10 mL) and concentrated HCl (40 µL) in the presence of palladium, 10% on carbon (32 mg), under a hydrogen atmosphere. The reaction medium was stirred for 24 h, then Millipore-filtered and evaporated in order to give compound T-18 (69 mg; 0.26 mmol) in the form of a white solid with a quantitative yield.

Rf: 0.46 (dichloromethane/methanol 80/20).

$^{19}$F NMR (CD₃OD, 282,5 MHz): −114.8 (1F; ddd; J=253 Hz; J=18 Hz; J=7 Hz); −118.7 (1F; ddd; J=253 Hz; J=24 Hz; J=6 Hz).

Mass (ESI⁻): 255.11[M−H]⁻; 291.08[M+Cl]⁻, 301.1[M+HCOO—]⁻.

Elemental Analysis Calculated: C, 46.87; H, 7.08. Found: C, 46.88; H, 7.09.

II—Biochemical Activity of the Compounds of the Invention

Procedure for the Study of Stability of Compounds T-16 and T-18

Compounds T-16 and T-18 were dissolved in D₂O and the resulting solutions were kept at room temperature. The stability of the compound was studied by $^{19}$F NMR and $^1$H NMR. A 24 weeks follow up for T-18 and 10 weeks follow up for T-16 has been performed without any degradation.

We have shown that difluorinated C-alkyl glycoside compounds T-16 and T-18 can be kept in aqueous solution at room temperature without undergoing any degradation.

Biological Activity: Expression of β-Galactosidase and Evaluation of the Toxicity to Bacteria The compounds T-16 and T-18 of the invention have been tested for their ability to induce the β-galactosidase expression in *Escherichia coli*. The toxicity to bacteria was also determined.

The assays have been performed according to the protocol below. Each compound was compared with well-known IPTG inducer and also with IBCG (isobutyl-C-galactoside, an IPTG analogue, in which the glycoside sulfur bond, has been replaced by a methylene).

a) Method
Preparation of Bacteria Culture:

The bacteria strain *E. coli* XL1—Blue MRF' Electroporation-competent cells (Stratagene #200158) containing pGEM-T vector was grown in LB medium adding with appropriate antibiotic (ampicillin). The starter culture was grown by inoculating plasmid containing cells in LB medium added with ampicillin and incubated overnight at 37° C. with shaking at 250 rpm. When culture reached the desired OD, the induction was started.

Induction of β-Galactosidase Expression:

For each assay the starter culture was appropriately diluted ($OD_{600}$=0.2) in 1.5 mL of LB medium with 3 µg/mL of ampicillin β-galactosidase expression is then induced by addition of either IPTG (Sigma I1284), IBCG or Compounds T-16 and T-18 to final concentrations of 0.5 or 1 mM. After this induction the cultures are incubated for 3 hours at 37° C. with shaking at 250 rpm.

Assays of β-Galactosidase Activity

The β-galactosidase activity was assayed by adding 0.5 mg/mL of the ortho 2-nitrophenyl-β-D-galactopyranoside (ONPG Sigma N1127) as chromogenic substrate. ONPG is hydrolyzed by β-galactosidase to yield galactose and ortho-Nitrophenol, which is yellow in color and absorbs light at 420 nm. The intensity of the color can be used to determine the β-galactosidase activity.

Absorbance was measured ($OD_{420nm}$) every hour during 8 hours after the substrate addition. The absorbance was plotted as a function of time representing the induction kinetic of β-galactosidase activity for each inducer and each concentration tested. Assays were performed as triplicate.

Toxicity:

The absorbance of the bacteria culture was measured ($OD_{600nm}$) every hour during 8 hours after the substrate addition. The absorbance was plotted as a function of time representing the toxicity for each inducer. The negative control (no toxicity) consists on an assay without inducer. Assays were performed as triplicate.

b) Results

FIG. 1 represents the β-galactosidase expression induced by compounds T-16, T-18, IPTG and IBCG at a concentration of 0.5 mM until 3 hours after the addition of ONPG substrate.

It was then demonstrated that all compounds induced β-galactosidase transcription. Compounds T-16 and T-18 are thus efficient inducers.

At concentration 0.5 mM, during 3 h following the substrate addition, the results are similar with compounds T-16 and T-18 and these results show that T-16 and T-18 are as effective inducers than IPTG but they are more effective inducers than IBCG.

Another experiment has been carried out with T-18 and IPTG at a concentration of 0.5 mM showing that T-18 is at least 3 times more effective than IPTG 8 h following substrate addition. This underlines the fact that compound T-18 remains effective overtime while IPTG's efficacy decrease.

Figure 2:
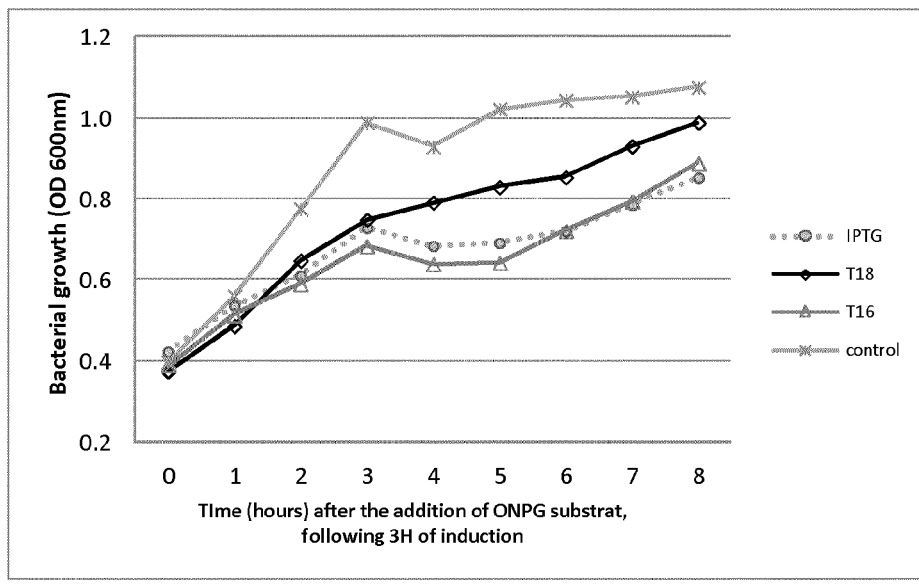
FIG. 2 represents the toxicity of compounds T-16, T-18 and IPTG used at 0.5 mM on *E. coli* culture, compared with a negative control (assay without inducer).

FIG. 2 represents the toxicity of the inducers used at 0.5 mM on *E. coli* culture, compared with a negative control (assay without inducer).

Compound T-18 (0.5 mM) is as toxic as IPTG until 3 h following the substrate addition, then T-18 is less toxic than IPTG until the end of the experiment, i.e. up to 8 h following the substrate addition.

Compound T-16 has a similar toxicity profile as the one observed with IPTG i.e. a medium toxicity throughout the assay.

The biological assays show that compounds T-16 and T-18 are effective inducers of lacZ promoter and could be used in inducing recombinant protein expression under lacZ promoter control. Moreover, these results suggest that compound T-18 is a better inducer than the reference IPTG when they are used at 0.5 mM for long inductions and is less toxic than IPTG for *E. coli*.

Biological Activity: Overtime Monitoring of Recombinant Protein Production

The compound T-18 of the invention has been tested for its ability to induce the expression of the soluble Green Fluorescent Protein UV (GFPuv) in *Escherichia coli* system. The assays have been performed according to the following protocol where the compound T-18 was compared with well-known IPTG inducer at different concentrations for 24 h.

a) Method

The Recombinant Protein induced was the Green Fluorescent Protein UV (GFPuv) with the following sequence of 246 amino acids:

MHHHHHHGSSKGEELFTGVVPILVELDGDVNGHKFSVSGEGEGDATYGK

LTLKFICTTGKLPVPWPTLVTTFSYGVQCFSRYPDHMKRHDFFKSAMPE

GYVQERTISFKDDGNYKTRAEVKFEGDTLVNRIELKGIDFKEDGNILGH

KLEYNYNSHNVYITADKQKNGIKANFKIRHNIEDGSVQLADHYQQNTPI

GDGPVLLPDNHYLSTQSALSKDPNEKRDHMVLLEFVTAAGITHGMDELYK

Properties: MW: 27 763 Da. Theoretical pI: 6.13—Theoretical Absorption coefficient: 0.788—Number of Cys: 2

Construction of One Expression Strain:
Construct GFPUV-pET30b/3 was transformed into BLR (DE3) *E. coli* expression strain.
Cultures were performed from one single colony in a semi-defined Riesenberg medium in order to produce a Research Cell Bank (20 tubes of 1 mL stored at <−70° C.).

Pre-cultures and Cultures Conditions:
Pre-cultures and cultures were performed in semi-defined Riesenberg medium, 50 mL and 250 mL flasks-scale, respectively. Medium was supplemented with 30 µg/mL of kanamycin.
Cultures were performed at 37° C. with shaking at 180 rpm.
Protein expression was induced by the addition of IPTG or T-18 at the same concentration when the $OD_{600nm}$ reached approximately 1.5.
2 temperatures conditions were performed (37° C. and 25° C.).
Induction kinetic was followed each hour during the first 8 hours of induction and after 24 hours of induction.
2×1 ml, of culture was centrifuged at 5,000 g, 4° C. during 10 min. for expression/solubility tests.

Expression/Solubility Test: Cellular Lysis and Fractionation
Bacteria pellets were resuspended in buffer 50 mM Tris-HCl, 300 mM NaCl, 1 mM DTT, 100 µg/mL, 1 µg/mL leupeptin, 1 μg/mL pepstatin, 5 U/mL benzonase, 2 mM MgCl$_2$ pH 8.0 at an equivalent OD600 nm of 8.

NB: As pellets becomes yellow/green when GFPuv is expressed, it was observed that GFPuv expression was low at 25° C. and only the cultured obtained after 24 hours of induction was lysed.

Cell lysis was performed by 3 cycles of freezing/thawing and then by lysozyme action (incubation 30 min. at room temperature).

Soluble and insoluble proteins were separated by centrifugation at 15,000 g, 4° C. during 30 min.

Analysis by SDS-PAGE Stained by Coomassie Blue

Sample: 10 μl deposit of suspension at equivalent OD$_{600nm}$=8.

The proteins were separated by SDS-PAGE 4-12%, and then colored by Coomassie blue.

Quantitative measurement by densitometry and comparison with standard range of proteins.

Quantity of proteins (μg) was plotted as a function of time representing the kinetic of induction of GFPuv expression for each inducer and/or concentration tested.

b) Results

The induction profile of GFPuv was evaluated for both IPTG and T-18 inducers at different concentrations. The effect of low concentrations and/or slow induction was particularly tested on the protein yield. Inductions were performed at 37° C. and both inducers IPTG and T-18 were tested at 0.5 mM, 0.1 mM, 0.05 mM, 0.01 mM and 0.005 mM for 24 h.

i. Analysis of Bacterial Growth During the Induction

Figure 3:
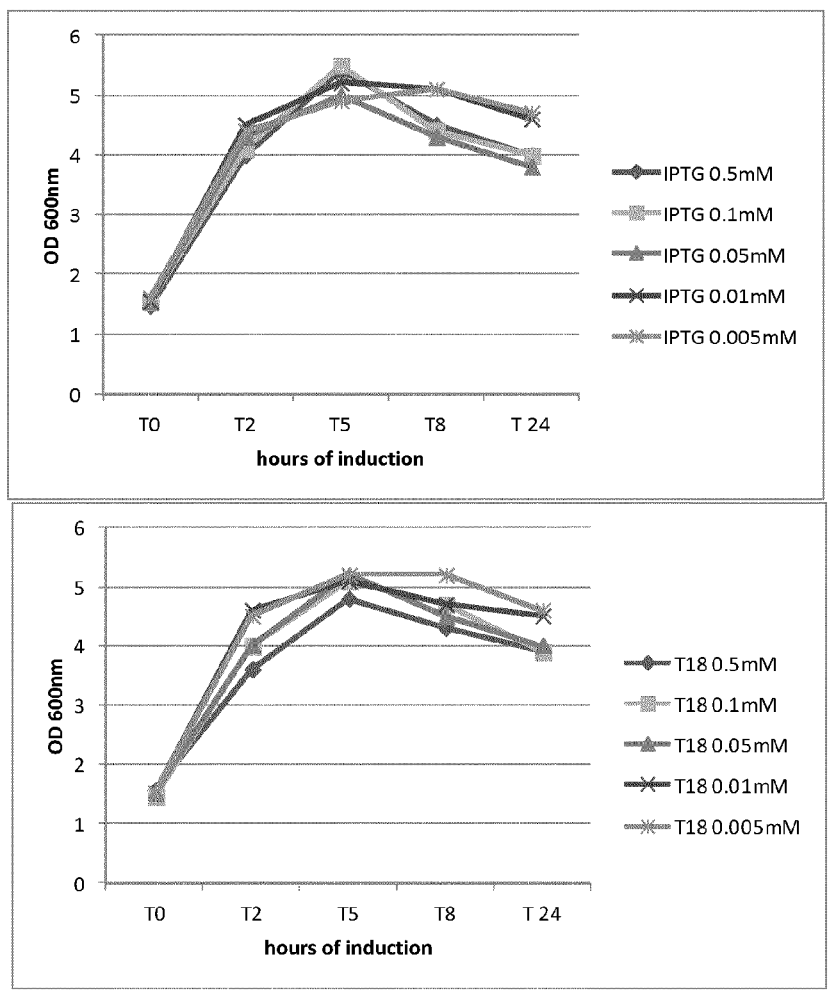
FIG. 3 represents the time course of bacterial growth during the inductions by IPTG or T-18 used at 0.5 mM, 0.1 mM, 0.05 mM, 0.01 mM and 0.005 mM.

The bacterial growth was followed by measuring the optical density (OD) at 600 nm. The inducers were compared at the same concentration no differences were observed in term of bacterial growth between IPTG and T-18 induction at the concentrations tested for 24 h (data not shown). The FIG. 3 showed that for each inducer the final OD$_{600nm}$ was higher when the induction was performed with a concentration of inducer equal or lower than 0.01 mM, from 8 hours of induction. A concentration effect was observed with T-18 from 2 hrs post induction and with IPTG from 8 hrs post induction.

ii. Quantification of GFPuv Production

Figure 4:
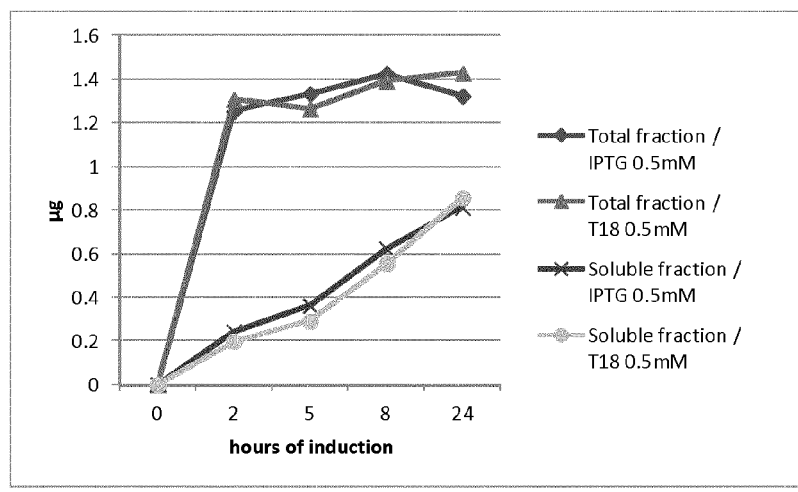
FIG. 4 represents the total and soluble fractions of recombinant GFPuv protein production induced by compound T-18 or IPTG used at 0.5 mM.
Figure 5:
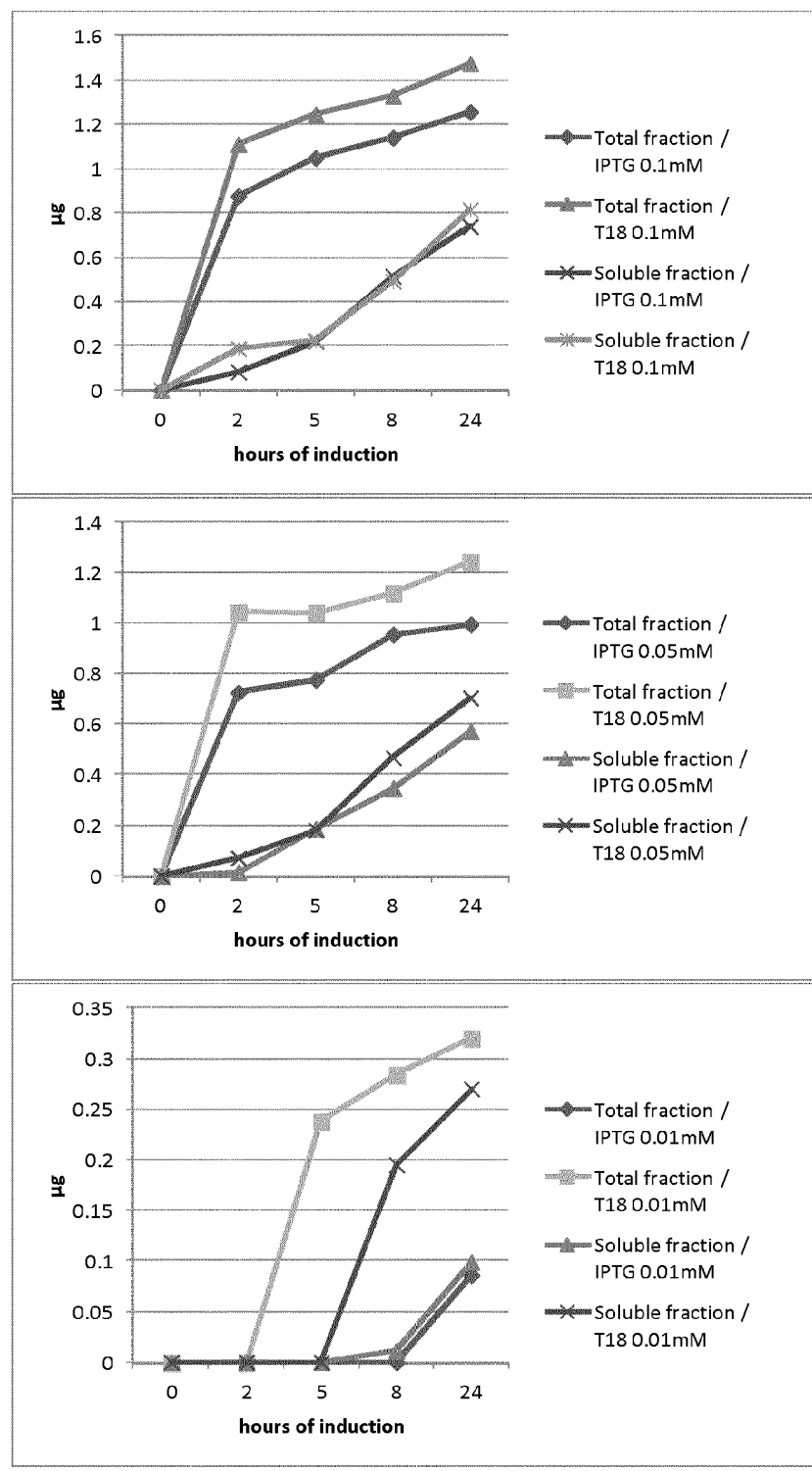
FIG. 5 represents the total and soluble fractions of recombinant GFPuv protein production induced by compound T-18 or IPTG used at 0.1 mM, 0.05 mM and 0.01 mM.

The quantities of GFPuv measured in total or soluble fractions were plotted as function of time post-induction in FIGS. 4 and 5:

Induction at 0.5 mM showed that after 24 hours the level of the soluble fraction of protein expressed was approximately 60% of the total fraction of protein produced. There was no difference between the two inducers (FIG. 4).

At low concentration of inducer (0.1 mM, 0.05 mM and 0.01 mM) the final quantity of GFPuv, produced with T-18 was higher than with IPTG whereas the quantity in the soluble fraction was equivalent for both the inducers (FIG. 5).

Figure 6:
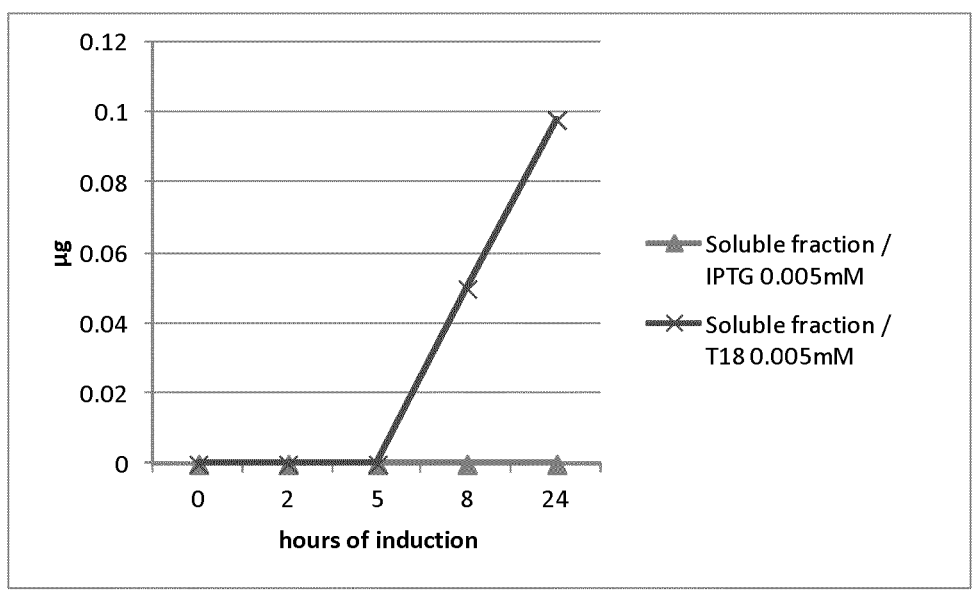
FIG. 6 represents the soluble fractions of recombinant GFPuv protein production induced by compound T-18 or IPTG used at 0.005 mM.

The GFPuv production in soluble fraction with inducer at very low concentration of 0.005 mM was illustrated in the FIG. 6 and showed that only T-18 is able to induce some protein expression due to its better stability. (Because of the high proportion of host cell proteins, the quantification of GFPuv in the total fraction was not possible).

c) Conclusion

The compound T-18 is a stable inducer more efficient than IPTG at low concentrations, equal or lower than 0.1 mM, to induce the expression of soluble recombinant protein GFPuv.

Abbreviations

| | |
|---|---|
| DMSO | Dimethylsulfoxide |
| eq. | Equivalent |
| ESI | Electrospray ionisation |
| g | Gram |
| Hz | Hertz |
| mg | Milligramme |
| MHz | Megahertz |
| min | Minute |
| mL | Milliliter |
| mmol | Millimole |
| NMR | Nuclear Magnetic Resonance |
| PCC | Pyridinium chlorochromate |
| Rf | Retardation factor |
| THF | Tetrahydrofurane |

The invention claimed is:

1. A compound of formula (I):

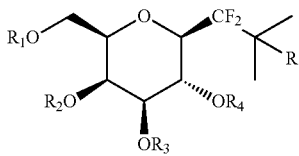

or a pharmaceutically acceptable salt thereof, wherein:

R represents H, OH or $OR^{19}$, $R_1$ represents H, $R^5$, $C(O)R^5$, $P(O)(OR^6)(OR^7)$, $SiR^8R^9R^{10}$, or a O-protecting group, and $R_2$, $R_3$ and $R_4$ represent, independently from one another, H, $R^{11}$, $C(O)R^{11}$, $SiR^{12}R^{13}R^{14}$, or a O-protecting group, or ($R_1$ and $R_2$) form together a chain —$CR^{15}R^{16}$— linking the oxygen atom carrying them, and/or ($R_3$ and $R_4$) or ($R_2$ and $R_3$) form a chain —$CR^{17}R^{18}$—linking the oxygen atom carrying them, with:

$R^5$ and $R^{11}$ representing, independently of one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, aryl-$(C_1-C_6)$alkyl or $(C_1-C_6)$alkyl-aryl group, this group being optionally substituted with one or more groups selected from a halogen atom, OH, COOH and CHO, $R^6$ and $R^7$ representing, independently of one another, a hydrogen atom or a $(C_1-C_6)$alkyl group, $R^8$, $R^9$, $R^{10}$, $R^{12}$, $R^{13}$, and $R^{14}$ representing, independently of each other, a $(C_1-C_6)$alkyl, aryl or aryl-$(C_1-C_6)$alkyl group, and $R^{15}$, $R^{16}$, $R^{17}$, and $R^{18}$ representing, independently of each other, a hydrogen atom, or a $(C_1-C_6)$alkyl, aryl or aryl-$(C_1-C_6)$alkyl group, $R^{19}$ representing $COCOOR^{20}$, and $R^{20}$ representing a $(C_1-C_6)$alkyl group.

2. The compound according to claim 1, wherein the O-protecting group is a Bn or MOM group.

3. The compound according to claim 1, wherein $R_1$ represents H, $R^5$, or $C(O)R^5$, with $R^5$ representing a $(C_1-C_6)$alkyl, aryl, or aryl-$(C_1-C_6)$alkyl group.

4. The compound according to claim 1, wherein $R_2$, $R_3$ and $R_4$ represent, independently from one another, H, $R^{11}$, or $C(O)R^{11}$, with $R^{11}$ representing a $(C_1-C_6)$alkyl, aryl, or aryl-$(C_1-C_6)$alkyl group.

5. The compound according to claim 1, wherein $R_1=R_2=R_3=R_4=H$.

6. The compound according to claim 1, wherein the compound is selected from the group consisting of

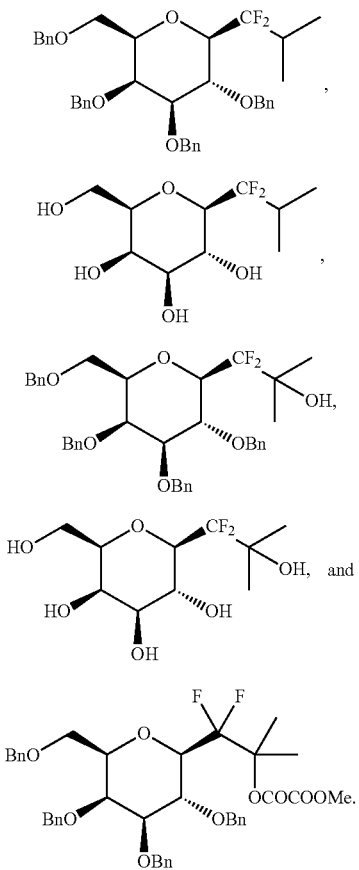

7. A process for preparing a compound according to claim 1 wherein R =OH, comprising reacting the ester function of a compound of formula (II):

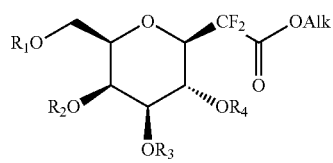

wherein $R_1$, $R_2$, $R_3$ and $R_4$ are as defined in claim 1 and Alk represents a ($C_1$-$C_6$)alkyl group, with MeLi or MeMgHal, Hal representing a halogen atom.

8. The process according to claim 7, wherein Hal represents a bromine or chlorine atom.

9. A process for preparing a compound according to claim 1 with R =$OR^{19}$, comprising reacting a compound of formula (I) according to claim 1 wherein R =OH with a compound of formula $R^{19}Cl$.

10. A process for preparing a compound according to claim 1 with R =H, comprising reducing a compound of formula (I) according to claim 1 for which R =$OR^{19}$.

11. A process for preparing a compound according to claim 1 with R =H, comprising hydrogenating the double bond of a compound of formula (III):

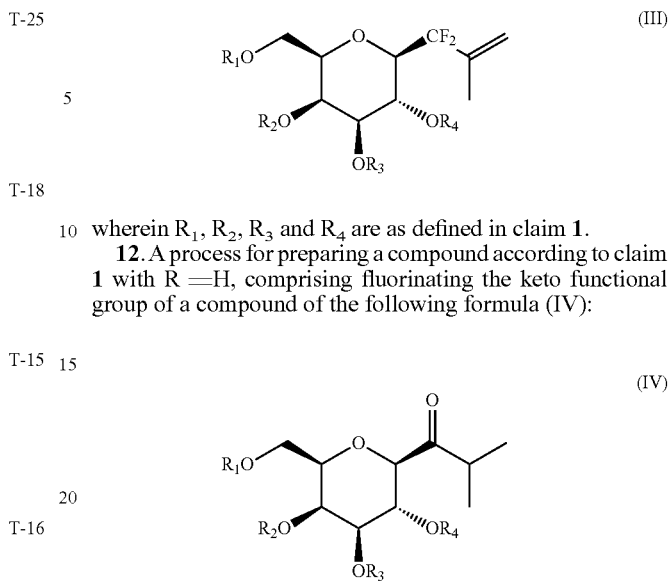

wherein $R_1$, $R_2$, $R_3$ and $R_4$ are as defined in claim 1.

12. A process for preparing a compound according to claim 1 with R =H, comprising fluorinating the keto functional group of a compound of the following formula (IV):

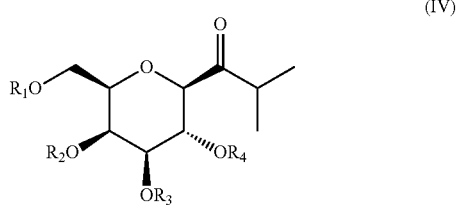

wherein $R_1$, $R_2$, $R_3$ and $R_4$ are as defined in claim 1.

13. A method for producing a protein comprising the following successive steps:
   a) transforming a host cell with a vector comprising a gene encoding said protein and a promoter, said promoter comprising at least one operator sequence capable of binding the LacI repressor, and
   b) growing the transformed cell of step a) in the presence of a compound according to claim 5.

14. The method according to claim 13, wherein the host cell is a bacterium.

15. The method according to claim 14, wherein the bacterium is *Escherichia coli*.

16. The method according to claim 12, wherein the operator sequence capable of binding the LacI repressor protein has the sequence sharing at least 60% identity with the sequence displayed in SEQ ID NO. 1: TGGAATTGTGAGCGGATAA-CAATT.

17. The method according to claim 16, wherein the operator sequence capable of binding the LacI repressor protein has the sequence sharing at least 75% identity with the sequence displayed in SEQ ID NO. 1: TGGAATTGTGAGCGGATAA-CAATT.

18. The method according to claim 17, wherein the operator sequence capable of binding the LacI repressor protein has the sequence sharing at least 85% identity with the sequence displayed in SEQ ID NO. 1: TGGAATTGTGAGCGGATAA-CAATT.

19. The method according to claim 18, wherein the operator sequence capable of binding the LacI repressor protein has the sequence sharing at least 95% identity with the sequence displayed in SEQ ID NO. 1: TGGAATTGTGAGCGGATAA-CAATT.

20. The method according to claim 19, wherein the operator sequence capable of binding the LacI repressor protein has the sequence sharing at least 99% identity with the sequence displayed in SEQ ID NO. 1: TGGAATTGTGAGCGGATAA-CAATT.

21. The method according to claim 13, further comprising after step b) an additional step of:
   c) isolating the protein from the transformed cell.

* * * * *

UNITED STATES PATENT AND TRADEMARK OFFICE
CERTIFICATE OF CORRECTION

PATENT NO. : 9,062,313 B2
APPLICATION NO. : 14/237490
DATED : June 23, 2015
INVENTOR(S) : Geraldine Deliencourt-Godefroy and Hyacinthe Fillon Page 1 of 1

It is certified that error appears in the above-identified patent and that said Letters Patent is hereby corrected as shown below:

IN THE SPECIFICATION

Column 12, line 43, please replace: "Lad" with "LacI"

Column 14, line 2, please replace: "Lad" with "LacI"

IN THE CLAIMS

Column 30, claim 18, line 48, please replace: "Lad" with "LacI"

Column 30, claim 20, line 58, please replace: "Lad" with "LacI"

Signed and Sealed this
Twenty-second Day of March, 2016

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Lac operator

<400> SEQUENCE: 1
tggaattgtg agcggataac aatt                                          24

<210> SEQ ID NO 2
<211> LENGTH: 246
<212> TYPE: PRT
<213> ORGANISM: Artificial sequence
<220> FEATURE:
<223> OTHER INFORMATION: Recombinant Green Fluorescent Protein UV
      (GFPuv)

<400> SEQUENCE: 2

Met His His His His His His Gly Ser Ser Lys Gly Glu Glu Leu Phe
1               5                   10                  15
```

```
Thr Gly Val Val Pro Ile Leu Val Glu Leu Asp Gly Asp Val Asn Gly
            20              25              30

His Lys Phe Ser Val Ser Gly Glu Gly Glu Gly Asp Ala Thr Tyr Gly
        35              40              45

Lys Leu Thr Leu Lys Phe Ile Cys Thr Thr Gly Lys Leu Pro Val Pro
    50              55              60

Trp Pro Thr Leu Val Thr Thr Phe Ser Tyr Gly Val Gln Cys Phe Ser
65              70              75              80

Arg Tyr Pro Asp His Met Lys Arg His Asp Phe Phe Lys Ser Ala Met
                85              90              95

Pro Glu Gly Tyr Val Gln Glu Arg Thr Ile Ser Phe Lys Asp Asp Gly
            100             105             110

Asn Tyr Lys Thr Arg Ala Glu Val Lys Phe Glu Gly Asp Thr Leu Val
        115             120             125

Asn Arg Ile Glu Leu Lys Gly Ile Asp Phe Lys Glu Asp Gly Asn Ile
    130             135             140

Leu Gly His Lys Leu Glu Tyr Asn Tyr Asn Ser His Asn Val Tyr Ile
145             150             155             160

Thr Ala Asp Lys Gln Lys Asn Gly Ile Lys Ala Asn Phe Lys Ile Arg
                165             170             175

His Asn Ile Glu Asp Gly Ser Val Gln Leu Ala Asp His Tyr Gln Gln
            180             185             190

Asn Thr Pro Ile Gly Asp Gly Pro Val Leu Leu Pro Asp Asn His Tyr
        195             200             205

Leu Ser Thr Gln Ser Ala Leu Ser Lys Asp Pro Asn Glu Lys Arg Asp
    210             215             220

His Met Val Leu Leu Glu Phe Val Thr Ala Ala Gly Ile Thr His Gly
225             230             235             240

Met Asp Glu Leu Tyr Lys
            245
```